United States Patent [19]

Ou

[11] Patent Number: 4,961,881
[45] Date of Patent: Oct. 9, 1990

[54] PROCESS FOR SEPARATING TRIGLYCERIDES AND REGENERATING ABSORBENT USED IN SAID SEPARATION PROCESS

[75] Inventor: John D. Ou, Naperville, Ill.

[73] Assignee: UOP, Des Plaines, Ill.

[21] Appl. No.: 156,857

[22] Filed: Feb. 17, 1988

[51] Int. Cl.⁵ ............................. C09F 5/10; C11B 3/00
[52] U.S. Cl. ............................... 260/428.5; 260/405.5
[58] Field of Search ...................................... 260/428.5

[56] References Cited

U.S. PATENT DOCUMENTS

| | | | |
|---|---|---|---|
| 4,049,688 | 9/1977 | Neuzil et al. | 260/428.5 |
| 4,529,551 | 7/1985 | Cleary et al. | 260/428.5 |
| 4,784,807 | 11/1988 | Zinnen | 260/428.5 |

Primary Examiner—Patrick P. Garvin
Assistant Examiner—E. D. Irzinski
Attorney, Agent, or Firm—Thomas K. McBride; John F. Spears, Jr.; Jack H. Hall

[57] ABSTRACT

The separation of polyunsaturated triglycerides from monounsaturated triglycerides and polyunsaturated fatty acids from monounsaturated fatty acids is performed by an adsorptive chromatographic process in liquid phase using silver- or copper-exchanged aluminosilicates as the adsorbent. The exchange ions limit deactivation of the desorbent to a substantial degree, but batchwise or continuous regeneration can be further practiced to maintain active adsorbent by treatment with hydrogen peroxide or an organic peroxide.

5 Claims, 8 Drawing Sheets

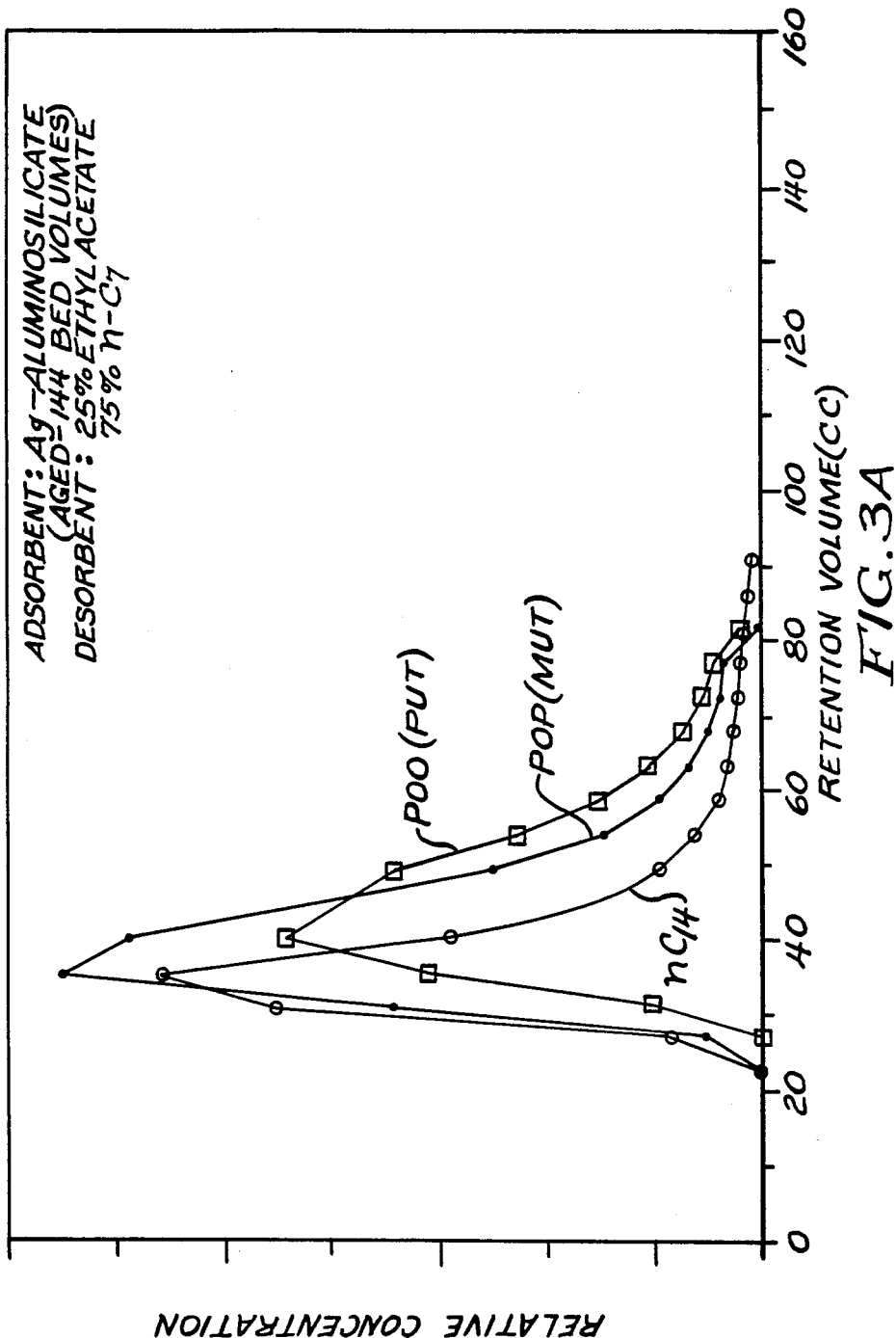

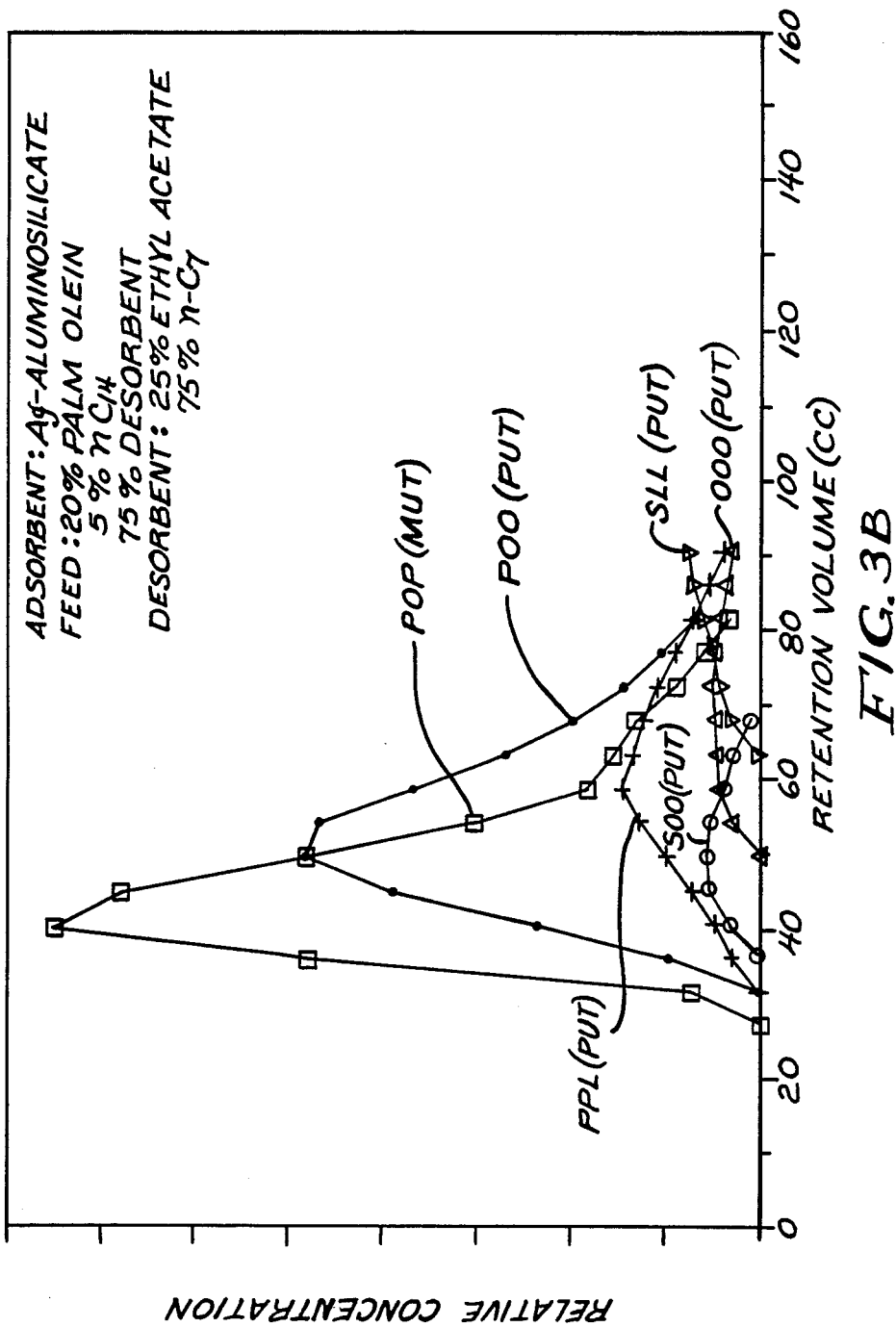

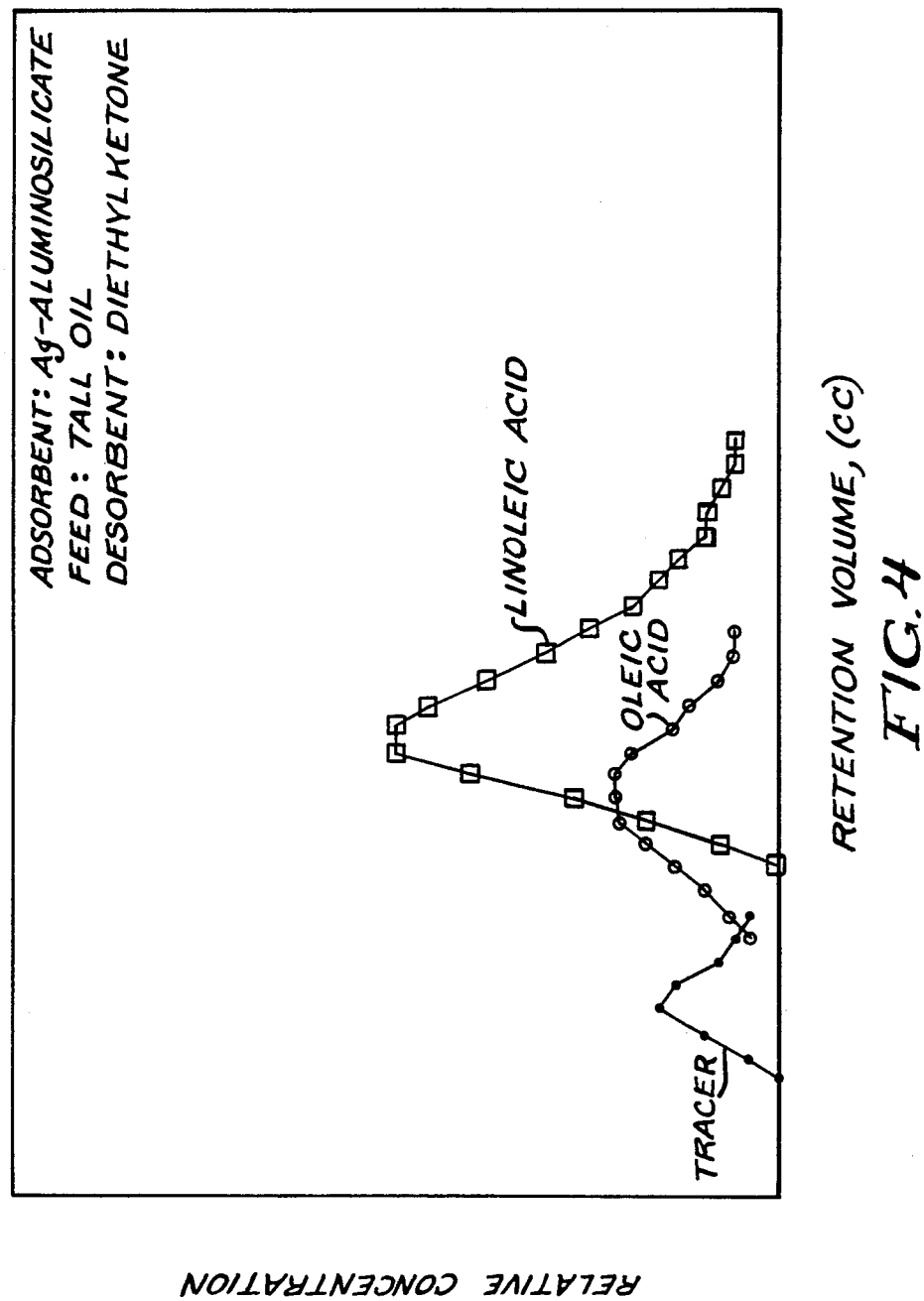

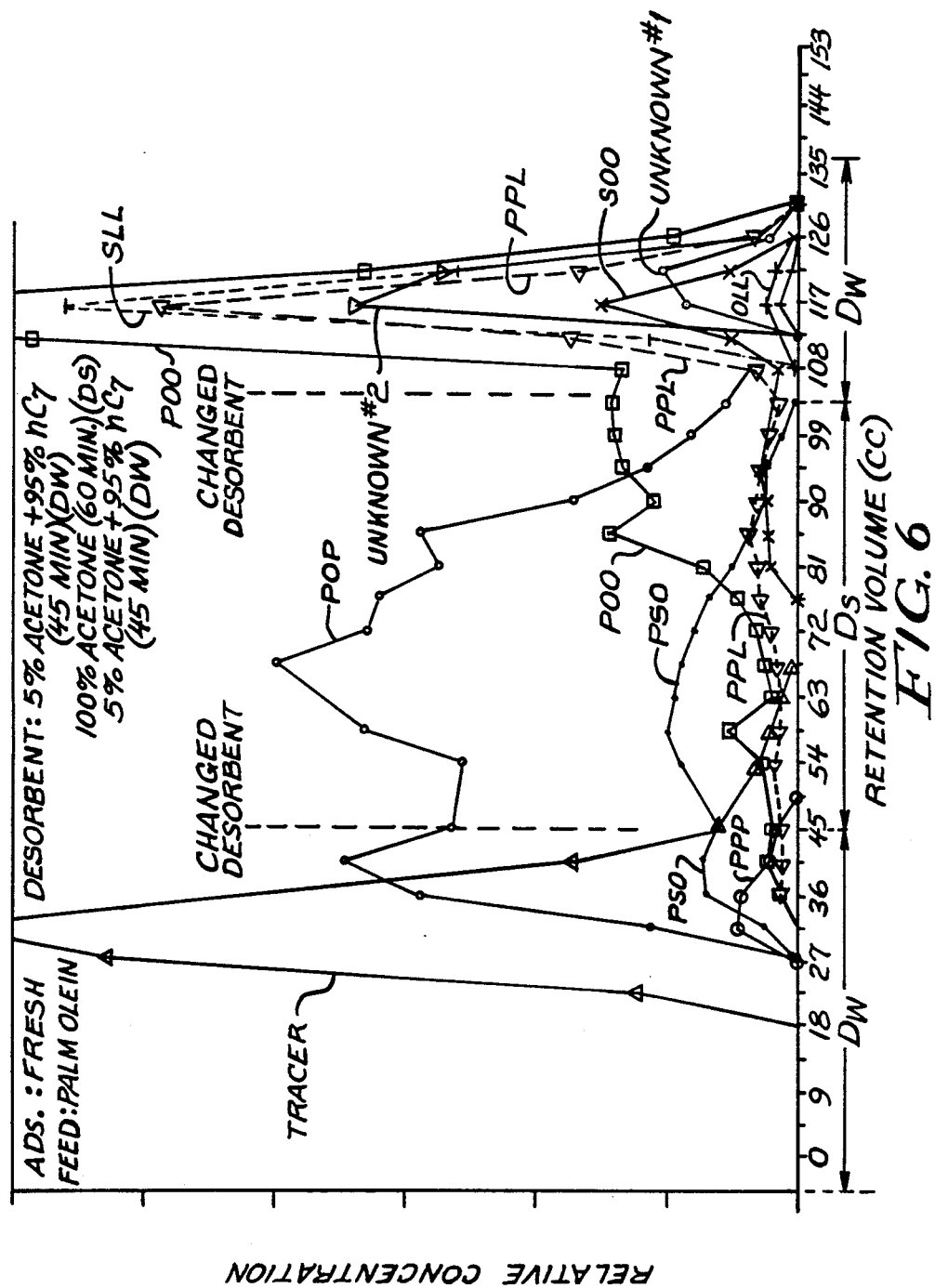

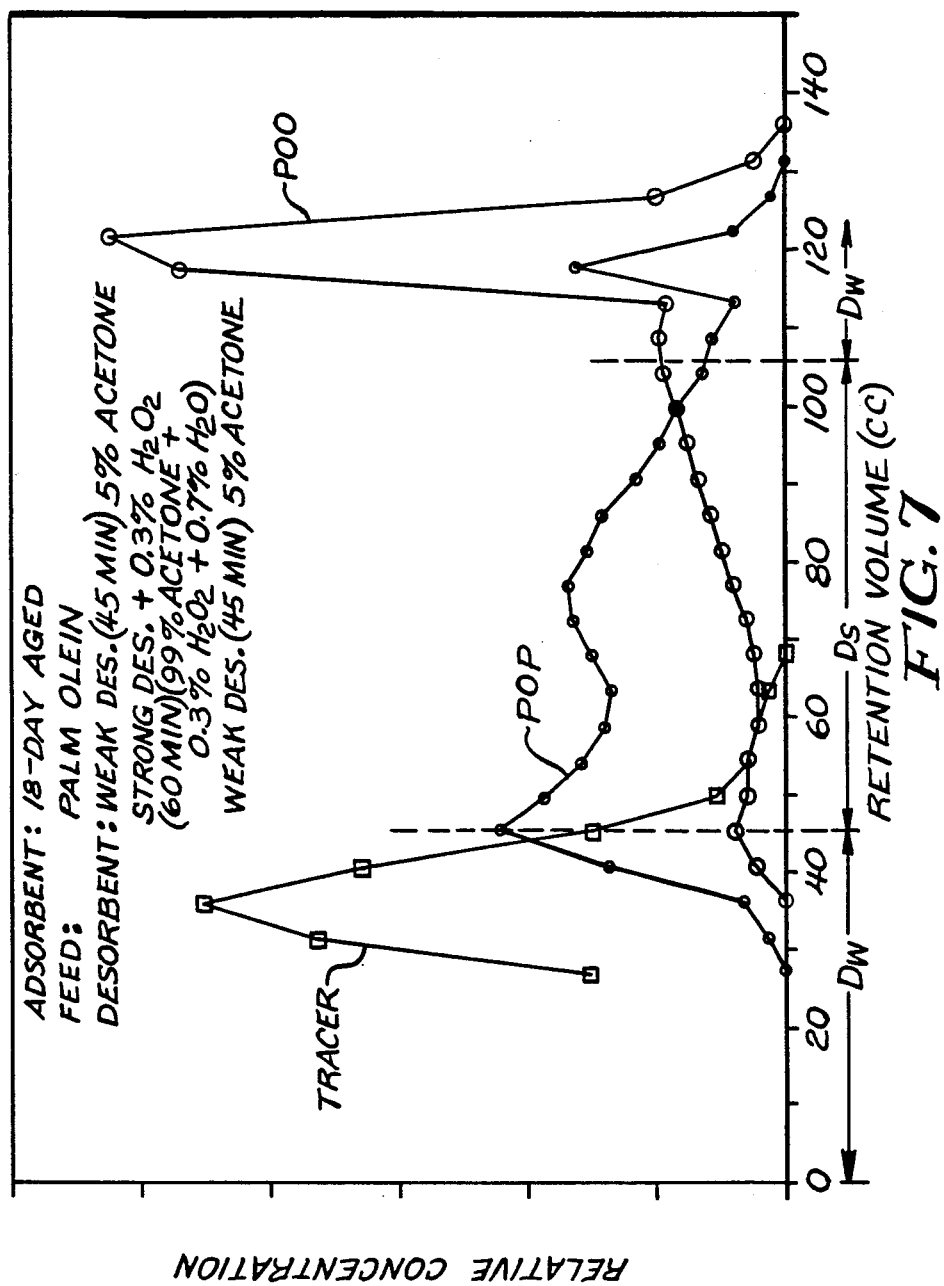

PROCESS FOR SEPARATING TRIGLYCERIDES AND REGENERATING ABSORBENT USED IN SAID SEPARATION PROCESS

FIELD OF THE INVENTION

The field of art to which this invention belongs is the solid bed adsorptive separation of triglycerides. More specifically, the invention relates to an improved process for separating monounsaturated triglycerides from polyunsaturated triglycerides and monounsaturated fatty acids from polyunsaturated fatty acids by a process which employs silver- or copper-exchanged aluminosilicate adsorbents and continuously or intermittently regenerates said adsorbents.

BACKGROUND OF THE INVENTION

The separation of many classes of compounds by selective adsorption on molecular sieves or zeolites as well as other adsorbents is well known. For example, as disclosed in U.S. Pat. No. 4,048,205 to Neuzil et al., methyl esters of fatty acids of various degrees of unsaturation may be separated from mixtures of esters of saturated and unsaturated fatty acids with X or Y zeolites exchanged with a selected cation. Further, in U.S. Pat. No. 4,353,838 to Cleary. et al., it is disclosed that monoethanoid fatty acids may be separated from diethanoid fatty acids with cross-linked polystyrenes, e.g. "Amberlite".

In a disclosure directly related to this invention, U.S. Pat. No. 4,277,412, the fractionation of fatty acid triglycerides by an adsorption process with permutite adsorbent and desorbent having specific solubility parameters is disclosed. The process, however, is not practical in many applications, since it requires the removal of certain contaminating adsorbent-deactivating reactants; otherwise, this adsorbent's life is extremely, and decidedly uneconomically, short, i.e., several hours or a day or two, at most.

U.S. Pat. No. 4,284,580 has a similar disclosure except that the adsorbent is surface-aluminated silica gel.

Neither suggests or discloses any reaction mechanism that might be responsible for deactivating the adsorbent. Furthermore, neither suggests or teaches a method for regenerating the adsorbent, either batchwise or continuously.

U.S. Pat. No. 3,696,107 discloses a process for separating para-xylene from a feed stream containing a mixture of C8 aromatics which employs the basic processing steps described in the first patent, a particular crystalline aluminosilicate adsorbent and a two-stage desorption operation in which a first desorbent stream contacts adsorbent in the desorption zone to effect the desorption of paraxylene from the adsorbent and a second desorbent stream contacts the adsorbent in the desorption zone to effect the pushing of desorbed paraxylenes from the interstitial void spaces between the adsorbent particles. One extract stream is withdrawn from the process.

U.S. Pat. Nos. 3,723,302, 4,006,197 and 4,036,745 each disclose a similar process for separating n-paraffins from isoparaffins using dual desorbents. In U.S. Pat. No. 4,006,197, sidecut streams taken from both extract and raffinate fractionator desorbents removed therein are recycled to the process. In this case, only one extract stream is removed. First and second desorbents are introduced, respectively, in zone II and between zones III and IV in U.S. Pat. Nos. 4,006,197 and 4,036,475. In U.S. Pat. No. 3,723,302, both desorbents enter into the desorption zone, but two extract streams are withdrawn. In U.S. Pat. No. 4,036,745, one or two extract streams may be withdrawn.

SUMMARY OF THE INVENTION

The improved process of separating triglycerides described herein has many potential uses for example, the fractionation of feed sources of triglycerides, e.g., palm olein and shea butter. Also oils, such as soybean oil, can be processed to give fractions which are enriched or depleted in unsaturation.

Another important application of my separation process resides in its utility in triglyceride synthesis. Cocoa butter, for example, is a high value natural product consisting predominantly of a mixture of particular triglycerides where the 2-position of glycerol is esterified with an oleyl group and the 1- and 3-positions are esterified with either the palmitoyl or the stearyl group. Both the palmitoyl and stearyl groups are fully saturated, i.e., no double bond unsaturation exists on either groups' hydrocarbon chain. However, the oleyl group is unsaturated to provide the glycerides with a single site of unsaturation. Cocoa butter, being primarily monounsaturated, has been referred to as a monounsaturated triglyceride (MUT). Cocoa butter is a predominant component in chocolate confections. It is believed that large quantities of triglycerides could be synthesized and used as cocoa butter extenders by reaction of free fatty acids with glycerol or by selective hydrogenation of polyunsaturated triglycerides, followed by separation of the resulting mixtures by the invention. Other uses for the polyunsaturated triglycerides which can be obtained by my process are in food applications, such as margarine and edible oils and soap making, etc.

The process incidentally (apparently by supplying oxygen-containing $H_2O_2$) removes colored contaminants, which detract from the value of the final product, from the desirable components. It is further contemplated that the process is valuable for separation of other saturated and unsaturated components from mixtures on the basis of degree of saturation, such as, fatty acids, esters of fatty acids, olefins from paraffins.

I have discovered a process for separating desirable compositions from mixtures of saturated and variously unsaturated triglycerides on the basis of degree of unsaturation using aluminosilicate adsorbents without resorting to prior treatments to remove adsorbent deactivating contaminants. The polyunsaturated triglycerides, which are adsorbed preferentially to other triglycerides, are concentrated in the extract. The monosaturated triglycerides, therefore, are removed from the mixture of triglycerides and are concentrated in the raffinate of the adsorptive separation apparatus.

The present invention is an improvement over the earlier disclosure of the separation of triglycerides on the basis of degree of unsaturation (U.S. Pat. No. 4,277,412) in that it is not necessary that the feed be essentially free of impurities, such as color bodies, trace metals, odor producing volatiles, catalyst, free fatty acids, etc.

Applicant's process also includes regeneration of the adsorbent, either continuously in the preferred embodiment or batchwise by the so-called "swing-bed" process. Part of applicant's discovery is that the particular deactivants are removed from the adsorbent or rendered harmless following a treatment of the adsorbent with hydrogen peroxide or other organic peroxide. It is hypothesized that deactivation of the adsorbent in this separation is being caused by short, highly unsaturated compounds of carotene origin produced during crude oil fractionation having structures derived from the following:

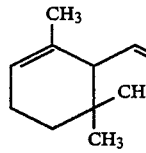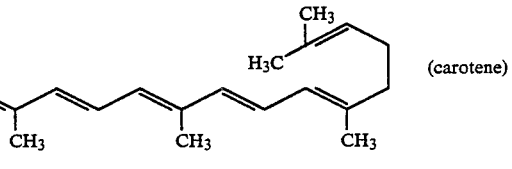 (carotene)

These compounds can become attracted to the silver ions on the surface or the adsorbent through the double bonds and eventually severely reduce the surface area available for adsorption of triglycerides. The hydrogen peroxide added to the adsorbent, either directly during batch regeneration of the bed at concentrations within the range of 0.1 wt. % to 5 wt. %, preferably 0.5 to 3% or continuously in the strong desorbent at concentrations within the range of 0.1 wt. % to 5 wt. %, preferably 0.1 to 0.3 wt. %, is believed to react with one or more of the double bonds to form epoxy compounds. Further details are provided hereinafter of the proposed process scheme for the swing-bed and continuous treatment of the adsorbent with hydrogen peroxide or an organic peroxide, e.g, peracetic acid.

A particular modification of the present invention is a process for separating monounsaturated triglycerides from a feed mixture comprising monounsaturated triglycerides and polyunsaturated triglycerides. The process comprises contacting the mixture at adsorption conditions with an adsorbent comprising aluminosilicate adsorbent exchanged with silver or copper ions. The more unsaturated triglycerides, e.g., polyunsaturated triglycerides (PUTs), are selectively adsorbed in preference to the more saturated triglycerides, e.g., monounsaturated triglycerides (MUTs). Next, the adsorbed triglycerides are recovered by a dual-desorbent treatment with a weak desorbent and a strong desorbent sometimes hereafter, $D_w$ and $D_s$, respectively. The weak desorbent may be selected from mixtures of an ester, e.g., ethyl acetate, propyl acetate, or a ketone, e.g., acetone, methylethyl ketone, diethyl ketone, etc. and a normal paraffin. The strong desorbent may be selected from organic solvents having the polarity parameters discussed below and mixtures thereof with hydrogen peroxide (0.1 to 5 wt. %, preferably 0.1 to 0.3%). The organic solvents include ketones, e.g., acetone, methylethyl ketone, diethyl ketone, alcohols, e.g., propanol, butanol and acetates, e.g., ethyl acetate, propyl acetate.

The steps of the continuous process are: (a) maintaining net fluid flow through a column of the adsorbent in a single direction, which column contains at least three zones having separate operational functions occurring therein and being serially interconnected with the terminal zones of the column connected to each other to provide a continuous connection of the zones; (b) maintaining an adsorption zone in the column, said zone adsorption defined by the adsorbent located between a feed input stream at an upstream boundary of the zone and a raffinate output stream at a downstream boundary of the zone; (c) maintaining a first purification zone immediately upstream from the adsorption zone, the first purification zone defined by the adsorbent located between a first desorbent input stream at an upstream boundary of the first purification zone and the feed input stream at a downstream boundary of the first purification zone; (d) maintaining a second purification zone immediately upstream from the first purification zone, said second purification zone defined by the adsorbent located between an extract output stream at an upstream boundary of the zone and the first desorbent input stream at a downstream boundary of the zone; (e) maintaining a desorption zone immediately upstream from said second purification zone, said desorption zone defined by the adsorbent located between a second desorbent input stream at an upstream boundary of the desorption zone and said extract output stream at a downstream boundary of said desorption zone; (f) passing a feed mixture containing contaminants which will deactivate the adsorbent into the adsorption zone at adsorption conditions to effect the selective adsorption of the polyunsaturated triglycerides by the adsorbent in the adsorption zone; (g) passing a first desorbent material into said first purification zone at desorption conditions to effect the displacement of the monounsaturated triglycerides or fatty acids from the adsorbent; (h) passing a second desorbent material including hydrogen peroxide or an organic peroxide, into said desorption zone at desorption conditions to effect the displacement of the polyunsaturated triglycerides from the adsorbent; (i) withdrawing an extract output stream comprising diglycerides, polyunsaturated triglycerides and second desorbent material from the desorption zone; (j) withdrawing a raffinate output stream comprising monounsaturated triglycerides and said first desorbent material from the adsorption zone; (k) periodically advancing through the column of adsorbent in a downstream direction with respect to fluid flow in the adsorption zone, the feed input stream, raffinate output stream, desorbent input streams, and extract output stream to effect the shifting of zones through the adsorbent and the production of extract output and raffinate output streams.

Additionally, a buffer, or second rectification, zone (IV) may be included. This serves the purpose of reducing the criticality of maintaining separation between zones I and III to avoid contamination of the extract with raffinate material.

In the practice of this modification, the first desorbent is a weak desorbent to remove the saturated triglycerides, MUTs and some PUTs having 2 double bonds. The second desorbent must be strong enough to remove tightly held contaminants, most of the PUTs having 2 double bonds and all PUTs having 3 or more double bonds and probably, olefinic substances which will otherwise remain in the adsorbent and quickly deactivate the adsorbent. A second extract outlet stream, may, if desired, be situated between the feed and the first desorbent inlet streams to separate the extract into components which may be desirable as product.

Other embodiments of my invention encompass details about feed mixtures, adsorbents, desorbent materials and operating conditions all of which are hereinafter disclosed in the following discussion of each of the facets of the present invention.

DESCRIPTION OF THE INVENTION

The following definitions of various terms used throughout this specification will be used in describing the operation, objects and advantages of the present invention.

A "feed mixture" is a mixture containing one or more extract components and one or more raffinate components to be fed to an adsorbent of the process. The term "feed stream" indicates a stream of feed mixture which passes to an adsorbent used in the process. The feed mixtures used herein are natural oils obtained from plant sources, such as safflower oil, palm oil and cocoa butter, which are mixtures of triglycerides. Safflower oil and cocoa butter are relatively simple mixtures. Safflower oil contains predominantly polyunsaturated triglycerides (PUT) such as trilinolein, while cocoa butter contains mostly monounsaturated triglycerides (MUT), such as 1,3-stearyl 2-oleyl triglyceride (SOS). Palm oil contains a more complex mixture of triglycerides, typically, predominantly PUT, such as 1-palmitoyl 2,3-oleyltriglyceride (POO), 1,3-palmitoyl 2-linoleic triglyceride (PLP), etc. and MUTs, such as 1,3-palmitoyl 2-oleyl triglyceride (POP), 1-palmitoyl 2-oleyl 3-stearyl triglyceride (POS), etc.

"MUTs" are mixtures of monounsaturated triglycerides. Where the predominant component(s) is (are) one (a plurality) of species, it will sometime be convenient to refer to the mixture by referring to the predominant species, e.g., dipalmitoyl oleyl triglyceride (a mixture of isomers or predominantly the designated isomer) as "POP" or "1,3-POP" (1,3-dipalmitoyl oleyl triglyceride), respectively. Also: "PSO"; "SOS"; "SOA" (A=arachidic; S=stearyl).

"PUTs" are mixtures of polyunsaturated triglycerides. Where a predominant species exists, they will be referred to, sometimes by the designation, e.g. "POO" (palmitoyl-dioleyl triglyceride) or "1,3-POO" (1,3-dioleyl-palmitoyl triglyceride). Likewise:

SLL (stearyl-dilinoleic triglyceride);
PPL (dipalmitoyl linoleic triglyceride;
SOO (stearyl-dioleyl triglyceride);
OLL (oleyl-dilinoleic triglyceride);
OOO (trioleyl triglyceride;
LLL (trilinoleic triglyceride;
PLL (palmitoyl dilinoleic triglyceride);
OOL (dioleyl-linoleic triglyceride);

An "extract component" is a type of compound or a compound that is more selectively adsorbed by the adsorbent while a "raffinate component" is a compound or type of compound that is less selectively adsorbed. In this process, polyunsaturated triglycerides (PUTs) are extract components and the monounsaturated triglycerides (MUTs) are raffinate components. The term "raffinate stream" or "raffinate output stream" means a stream through which a raffinate component is removed from an adsorbent. The composition of the raffinate stream can vary from essentially 100% desorbent material (hereinafter defined) to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. Although it is possible by the process of this invention to produce high-purity extract product (hereinafter defined) or a raffinate product (hereinafter defined) at high recoveries, it will be appreciated that an extract component is never completely adsorbed by the adsorbent, nor is a raffinate component completely nonadsorbed by the adsorbent. Therefore, small amounts of a raffinate component can appear in the extract stream, and likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, in one embodiment, the ratio of the concentration of the more selectively adsorbed triglycerides to the concentration of less selectively adsorbed triglycerides will be highest in the extract stream, next highest in the feed mixture, and lowest in the raffinate stream. Likewise, the ratio of the less selectively adsorbed triglycerides to the more selectively adsorbed triglycerides will be highest in the raffinate stream, next highest in the feed mixture, and the lowest in the extract stream. The term "desorbent material" shall mean generally a material capable of desorbing an extract component. The term "desorbent stream" or "desorbent input stream" indicates the stream through which desorbent material passes to the adsorbent. When the extract stream and the raffinate stream contain desorbent materials, at least a portion of the extract stream and preferably at least a portion of the raffinate stream from the adsorbent will be passed to separation means, typically fractionators, where at least a portion of the desorbent material will be separated at separation conditions to produce an extract product and a raffinate product. The terms "extract product" and "raffinate product" mean products produced by the process containing, respectively, an extract component and a raffinate component in higher concentrations than those found in the respective extract stream and the raffinate stream. The term "selective pore volume" of the adsorbent is defined as the volume of the adsorbent which selectively adsorbs extract components from a feed mixture. The term "nonselective void volume" of an adsorbent is the volume of an adsorbent which does not selectively retain an extract component from a feed mixture. This volume includes the cavities of the adsorbent which contain no adsorptive sites and the interstitial void spaces between adsorbent particles. The selective pore volume and the nonselective void volume are generally expressed in volumetric quantities and are of importance in determining the proper flow rates of fluid required to be passed into the process for efficient operations to take place for a given quantity of adsorbent.

The term "desorbent material" as used herein shall mean any fluid substance capable of removing a selectively adsorbed feed component from the adsorbent. Generally, in a swing-bed system in which the selectively adsorbed feed component is removed from the adsorbent by a purge stream, desorbent material selection is not too critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which employ zeolitic or nonzeolitic adsorbents and which are generally operated continuously at substantially constant pressures and temperatures to ensure liquid phase, the desorbent material relied upon must be judiciously selected to satisfy several criteria. First, the desorbent material must displace the extract components from the adsorbent with reasonable mass flow rates without itself being so strongly adsorbed as to unduly prevent the extract from displacing the desorbent material in a following adsorption cycle. Expressed in terms of the selectivity (hereinafter discussed in more detail), it is preferred that the adsorbent be more selective for the extract component with respect to a raffinate component than it is for the desorbent material with respect to a raffinate component. Secondly, desorbent materials must be compatible with the particular adsorbent and the particular feed mixture. More specifically, the desorbent must not react with either the adsorbent or any component of the feed material and must not reduce or destroy the critical selectivity of the adsorbent for the extract components with respect to the raffinate component. Desorbent materials to be used in the process of this invention should additionally be substances which are easily separable from the feed mixture that is passed into the process. After desorbing the extract components of the feed, both desorbent material and the extract components are typically removed in admixture from the adsorbent. Likewise, one or more raffinate components is typically withdrawn from the adsorbent in admixture with desorbent material and without a method of separating at least a portion of desorbent material, such as distillation, neither the purity of the extract product nor the purity of the raffinate product would be very high. It is, therefore, contemplated that any desorbent material used in this process will have a substantially different average boiling point than that of the feed mixture to allow separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture.

The desorbent materials used in the process of this invention should also be materials that are easily separated from the feed mixture. Both the raffinate stream and the extract stream are removed from the adsorbent in admixture with desorbent materials. Without a method of separating these desorbent materials, the purity of the extract components and the raffinate components if their recovery, is desired would not be very high nor would the desorbent materials be available for reuse in the process. It is contemplated, therefore, that the desorbent materials will have a different boiling range than the feed mixture fed to the adsorbent which would allow fractionation to be used to separate the raffinate and extract components and allow recovery of the desorbent materials for possible reuse in the process.

In the preferred isothermal, isobaric, liquid-phase operation of the process of this invention, ketones, e.g., methylethyl ketone, methyl isobutyl ketone, diethyl ketone and acetone and mixtures thereof are the preferred strong desorbent, with mixtures thereof with 0.1 to 5%, with 0.1 to 1% $H_2O_2$ being more preferred and 0.1 to 0.3% $H_2O_2$ most preferred. Paraffinic hydrocarbons, e.g. hexane and isooctane, or mixtures thereof with from 1% up to about 5 or 10%, preferably 3 to 7% of a ketone are the preferred weak desorbents. In addition to hydrogen peroxide, other organic peroxidic compounds can be used to remove the deactivating materials from the adsorbent, thereby regenerating the adsorbent. Other organic peroxidic compounds include organic per acids, such as peracetic acid, perbenzoic acid and performic acid, and organic peroxides, such as benzoyl peroxide, etc.

The prior art has recognized that certain characteristics of adsorbents are highly desirable, if not absolutely necessary, to the successful operation of a selective adsorption process. Among such characteristics are: adsorptive capacity for some volume of an extract component per volume of adsorbent; the selective adsorption of an extract component with respect to a raffinate component and the desorbent material; and sufficiently fast rates of adsorption and desorption of the extract components to and from the adsorbent.

Capacity of the adsorbent for adsorbing a specific volume of one or more extract components is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, $(\beta)$, for one component as compared to another component. Relative selectivity can be expressed not only for one feed component as compared to another but can also be expressed between any feed mixture component and the desorbent material. The selectivity, ( ), as used throughout this specification is defined as the ratio of the two components of the adsorbed phase over the ratio of the same two components in the unadsorbed phase at equilibrium conditions.

Relative selectivity is shown as Equation 1 below:

$$\text{Selectivity} = (\beta) = \frac{[\text{vol. percent } C/\text{vol. percent } D]_A}{[\text{vol. percent } C/\text{vol. percent } D]_U} \quad \text{Equation 1}$$

where C and D are two components of the feed represented in volume percent and the subscripts A and U represent the adsorbed and unadsorbed phases, respectively. The equilibrium conditions are determined when the feed passing over a bed of adsorbent does not change composition after contacting the bed of adsorbent. In other words, there is no net transfer of material occurring between the unadsorbed and adsorbed phases.

Where selectivity of two components approaches 1.0 there is no preferential adsorption of one component by the adsorbent with respect to the other; they are both adsorbed (or nonadsorbed) to about the same degree with respect to each other. As the $(\beta)$ becomes less than or greater than 1.0 there is a preferential adsorption by the adsorbent for one component with respect to the other. When comparing the selectivity by the adsorbent of one component C over component D, a ($\beta$) larger than 1.0 indicates preferential adsorption of component C within the adsorbent. A ($\beta$) less than 1.0 would indicate that component D is preferentially adsorbed leaving an unadsorbed phase richer in component C and an adsorbed phase richer in component D. While separation of an extract component from a raffinate component is theoretically possible when the selectivity of the adsorbent for the extract component with respect to the raffinate component just exceeds a value of 1.0, it is preferred that such selectivity have a value approaching or exceeding 2. Like relative volatility, the higher the selectivity the easier the separation is to perform. Higher selectivities permit a smaller amount of adsorbent to be used in the process. Ideally, desorbent materials should have a selectivity equal to about 1 or less than 1 with respect to all extract components so that all of the extract components can be extracted as a class and all raffinate components clearly rejected into the raffinate stream.

The third important characteristic is the rate of exchange of the extract component of the feed mixture material with the desorbent material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and, therefore, permit a reduction in the operating cost of the process. With faster rates of exchange, less desorbent material has to be pumped through the process and separated from the extract stream for reuse in the process.

The adsorbents of this invention are synthetic, amorphous aluminosilicates known as permutites, described generally in Breck, D. W., *Zeolite Molecular Sieves*, John Wilsey & Sons, New York, 1974, pp 11–13 and also in the aforementioned U.S. Pat. No. 4,277,412. Detailed directions for making the adsorbents are given in the Examples appearing below. They are characterized by homogeneity with respect to the silicon and aluminum atoms, a silicon to aluminum ratio of from about 2:1 to about 20:1 and a surface area (B.E.T.) (basis: 100% sodium exchange) of at least about 100 m$^2$/g, capable of exchanging ions for others, size ranging from 20–60 mesh and water content less than 10% (by wt.).

The adsorbent may be prepared according to the following procedure: Dilute 190 pounds waterglass (30% SiO$_2$) and 76.3 pounds sodium aluminate (23% Al$_2$O$_3$) in separate containers with deionized water, maintaining the solutions at about 5°–10° C.; add the sodium aluminate to the waterglass; the mixture gels within about 30 seconds; crush the gel and mix it with equal volume of water; add nitric acid to the gel/water slurry to bring the pH to about 6.0; filter the slurry to remove the liquid and dry the filter cake at 200° F. for 10 hours and then at 300° F. for 4 hours; grind the dried gel to 30/50 mesh particles; wash the ground gel with 0.01M nitric acid to remove residual alkalinity; ion exchange the gel by recycling a 0.4M silver nitrate solution through the bed; rinse the exchanged adsorbent with deionized water and dry at 70°–90° C. for 18 hours. The adsorbent so prepared has a typical composition of 15 to 30, preferably 20 to 30, wt. % Ag$_2$O, 15 to 30 wt. % Al$_2$O$_3$ and 40 to 60 wt. % SiO$_2$. The surface area ranges from 200 to 250M$^2$/g. The silver-exchanged aluminosilicate cannot be employed in a conventional one-adsorbent-and-one-desorbent adsorption separation process due to the severe adsorbent deactivation problem. Pulse test results for an adsorbent sample of Ag-exchanged aluminosilicate adsorbent indicate that after about 10 bed volumes of 20 wt. % palm olein feed has been treated in the process, the selectivity decreases from about 2.0 to about 1.5 and further deactivation is predicted to be so rapid as to make commercialization of the process impossible. Furthermore, deactivation is so rapid that conventional adsorbent bed regeneration is impractical due to too-frequent process interruptions. On the other hand, regeneration can be accomplished, with the peroxide treatment described herein, by one of the two methods previously mentioned, of which dual desorbents and continuous peroxide treatment are preferred.

In order to test various adsorbents and desorbent material with a particular feed mixture to measure the adsorbent characteristics of adsorptive capacity and selectivity and exchange rate, a dynamic testing apparatus is employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze "on-stream" the effluent stream leaving the adsorbent chamber.

A pulse test, performed using this apparatus and the following general procedure, is used to determine selectivities and other data for various adsorbent systems. The adsorbent is filled to equilibrium with a particular desorbent by passing the desorbent material through the adsorbent chamber. At a convenient time, a pulse of feed containing known concentrations of a nonadsorbed tracer, for instance, and of the particular feed material all diluted in desorbent is injected for a duration of several minutes. Desorbent flow is resumed, and the tracer and the triglycerides are eluted as in a liquid-solid chromatographic operation. In the present invention the desorbent is injected into the pulse test column in three steps: first, a weak desorbent at 1.5 cc/min. for 45 min.; next, strong desorbent at 1.5 cc/min. for 60; finally, additional weak desorbent at 1.5 cc/min until the remaining MUTs, PUTs, unknowns and D$_s$ are removed. The effluent can be analyzed by on-stream chromatographic equipment and traces of the envelopes of corresponding component peaks developed. Alternately, effluent samples can be collected periodically and later analyzed separately by gas or liquid chromatography.

From information derived from the chromatographic traces, adsorbent performance can be rated in terms of capacity index for an extract component, selectivity for the triglycerides with respect to the other, and the rate of desorption of an extract component by the desorbent. The capacity index may be characterized by the distance between the center of the peak envelope of the selectively adsorbed triglycerides and the peak envelope of the tracer component or some other known reference point. It is expressed in terms of the volume in cubic centimeters of desorbent pumped during this time interval. Selectivity, ($\beta$), for an extract component with respect to a raffinate component may be characterized by the ratio of the distance between the center of an extract component peak envelope and the tracer peak envelope (or other reference point) to the corresponding distance between the center of a raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

In this process, two desorbent materials are employed. A first desorbent material sometimes referred to herein as the "weak" desorbent, desorbs the lightly-held product triglycerides (MUTs) from the adsorbent. The weak desorbent, which may be an ester or a ketone mixed with an n-paraffin, is characterized by a solubility parameter (Polar Component) ($S_p$) (Kirk-Othmer Encyclopedia of Chemical Technology, 2nd. Ed. Supple. Vol. pp 889–910 of 0.2–0.4 and a solubility parameter (Hydrogen Bonding Component) ($S_h$) (ibid) of 0.1–0.3. Thus, a separation is achieved between the MUTS and the strongly adsorbed components, PUTs and other contaminants, which cannot be desorbed by the weak desorbent. To remove the PUTs and feed contaminants from the adsorbent, a second desorbent, hereinafter sometimes termed the strong desorbent, is used. The strong desorbent is characterized by solubility parameters $S_p$, from 1.3 to 13, preferably 1.3–5.0, and $S_h$, from 0.8 to 21, preferably 0.8–5.

Typically, adsorbents used in separative processes contain the adsorbent material dispersed in an amorphous binder material or inorganic matrix, having channels and cavities therein which enable liquid access to the adsorbent material. Also, in the case of the present invention, the adsorbent may be binderless. Silica, alumina, bentonite, or mixtures thereof are typical of such inorganic matrix materials. The binder aids in forming or agglomerating the adsorbent particles. The adsorbent may, thus be in the form of particles such as extrudates, aggregates, tablets, macrospheres or granules having a desired particle range, preferably from about 20 to about 60 mesh (Standard U.S. Mesh).

The adsorbent may be employed in the form of a dense fixed bed which is alternately contacted with a feed mixture and a desorbent material in which case the process will be only semicontinuous. In another embodiment, a set of two or more static beds of adsorbent may be employed with appropriate valving so that a feed mixture can be passed through one or more adsorbent beds of a set while a desorbent material is passed through one or more of the other beds in a set. The flow of a feed mixture and a desorbent material may be either up or down through an adsorbent in such beds. Any of the conventional apparatus employed in a static bed fluid-solid contacting may be used.

Moving bed or simulated moving bed flow systems, however, have a much greater separation efficiency than fixed bed systems and are, therefore, preferred. In the moving bed or simulated moving bed processes, the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. In such a system, it is the progressive movement of multiple liquid access points down a molecular sieve chamber that simulates the upward movement of molecular sieve contained in the chamber. Reference can also be made to D. B. Broughton's U.S. Pat. No. 2,985,589, in which the operating principles and sequence of such a flow system are described, and to a paper entitled, "Continuous Adsorptive Processing—A New Separation Technique," by D. B. Broughton presented at the 34th Annual Meeting of the Society of Chemical Engineers at Tokyo, Japan on Apr. 2, 1969, both references incorporated herein by reference for further explanation of the simulated moving bed countercurrent process flow scheme.

Another embodiment of a simulated moving bed flow system suitable for use in the process of the present invention is the concurrent high efficiency simulated moving bed process disclosed in U.S. Pat. No. 4,402,832 to Gerhold, incorporated by reference herein in its entirety.

It is contemplated that at least a portion of the raffinate output stream will pass into a separation means wherein at least a portion of the desorbent material can be separated at separating conditions to produce a raffinate product containing a reduced concentration of desorbent material. Preferably, but not necessary to the operation of the process, at least a portion of the extract output stream will also be passed to a separation means wherein at least a portion of the desorbent material can be separated at separating conditions to produce a desorbent stream which can be reused in the process and an extract product containing a reduced concentration of desorbent material. Typically, the concentration of desorbent material in the extract product and the raffinate product will be less than about 5 vol. % and more preferably less than about 1 vol. %. The separation means will typically be a fractionation column, the design and operation of which is well known to the separation art.

Although both liquid and vapor phase operations can be used in many adsorptive separation processes, liquid-phase operation is preferred for this process because of the high boiling points of the triglycerides. Adsorption conditions will include a temperature range of from about 20° C. to about 250° C. with about 50° C. to about 100° C. being more preferred and a pressure sufficient to maintain liquid phase. Desorption conditions will include the same range of temperatures and pressure as used for adsorption conditions.

The size of the units which can utilize the process of this invention can vary anywhere from those of pilot-plant scale (see for example U.S. Pat. No. 3,706,812) to those of commercial scale and can range in flow rates from as little as a few cc's an hour up to many thousands of gallons per hour.

The following examples are presented for illustration purposes and more specifically are presented to illustrate the selectivity relationships that make the process of the invention possible. Reference to specific cations, desorbent materials, feed mixtures and operating conditions is not intended to unduly restrict the scope and spirit of the claims attached hereto.

BRIEF DESCRIPTION OF THE DRAWINGS

FIGS. 2, 3a, 3b and 4–7 are chromatographic traces of the pulse tests described in Examples I-VI, illustrating the separation of various feeds with the desorbents of the invention.

DESCRIPTION OF THE DRAWINGS

Figure 1:
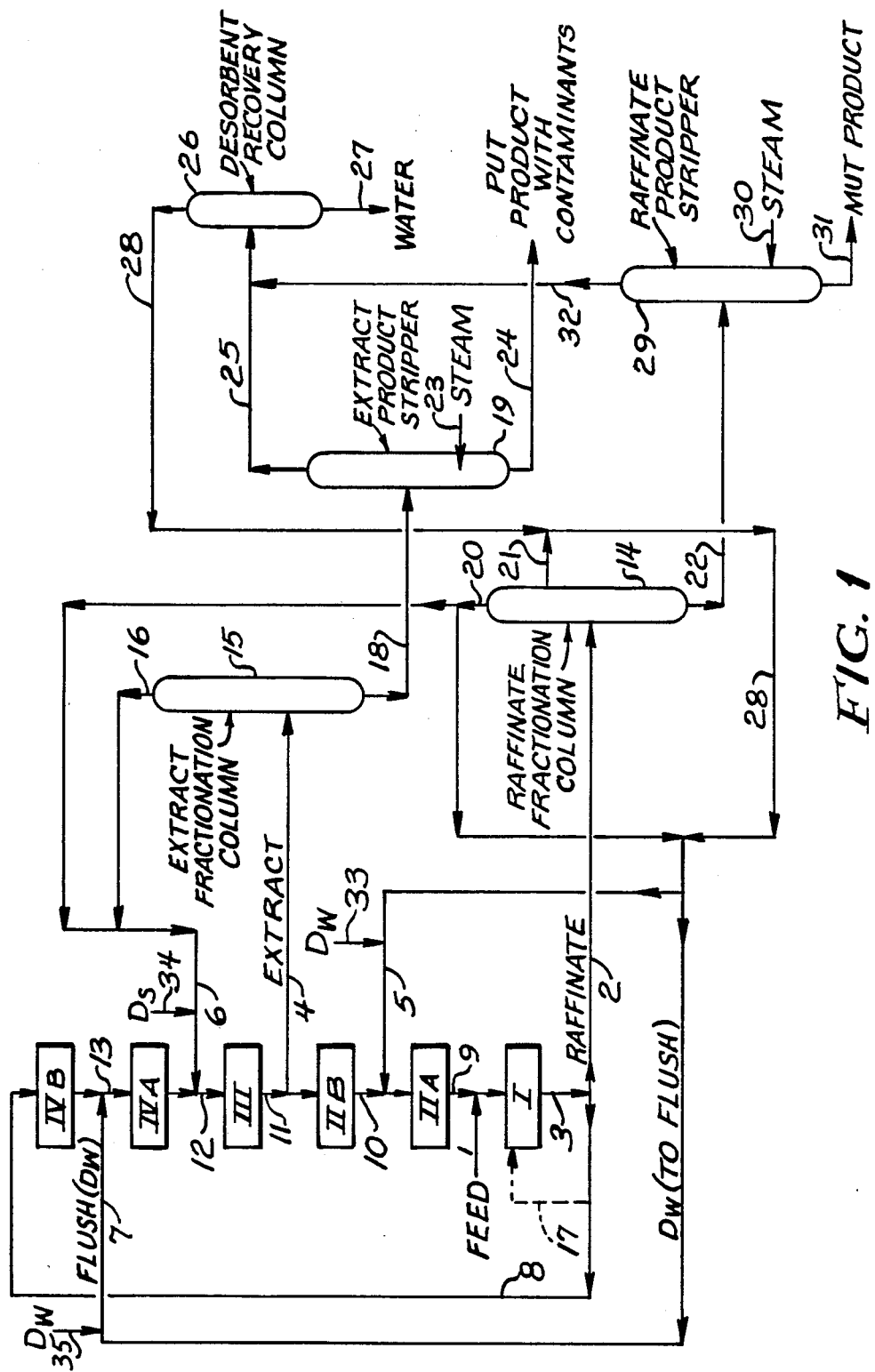
FIG. 1 is a flow diagram of the separation process of the invention.

FIG. 1 illustrates schematically the process of this invention. Basically, the drawing shows six separate operating zones and five separate fractionation means along with input and output streams and connecting conduits. Adsorption zone I, purification zones IIA and IIB, desorption zone III and optional buffer zones IVA and IVB are used to separate polyunsaturated triglycerides (PUTs) from monounsaturated triglycerides (MUTs) to produce an extract output stream containing a higher concentration of PUTs than the feed and a raffinate output stream containing an increased concentration of MUTs.

In order to simplify the explanation of the various operations taking place within the process, it is necessary to define the process in terms of separate operational zones. Three basic operational zones are utilized—namely, an adsorption zone, a rectification zone and a desorption zone. In some instances, an optional fourth operational zone referred to as a buffer zone is utilized, but this zone is not necessary to enable a separation to occur. In the purification zone II, the operation can be broken down into two essential steps. In zone IIA, raffinate components in the selective and nonselective voids are displaced by the first, weak, desorbent. In zone IIB, the weak desorbent in selective and nonselective voids is displaced by the extract from zone III. Likewise, in the buffer zone IV, the operation is broken down into two essential steps: in zone IVA, the strong desorbent ($D_s$) is removed by a flush stream of weak desorbent to ensure that $D_s$ does not enter the raffinate stream; in zone IVB, the weak desorbent ($D_w$) is partially desorbed and removed by the raffinate recycle stream.

The four zones are stationary beds of solid adsorbent particles but may in other instances consist of a series of one or more individual chambers connected in a serial manner. Each of the individual zones may be single chamber or a series of beds stacked upon one another in a column making up a zone. Thus, in some instances each of the above zones would contain the same general quantity of adsorbent and have the same general physical dimensions, but in other instances some zones may require more adsorbent than other zones. The indicated overall net liquid flow through the zones is in a downward direction, but in some instances a zone may be operating in a manner to allow flow of fluid for a certain period of time in a direction opposite to the overall net flow of fluid. The adsorbent particle flow can be considered to be in an upward direction to help in understanding the processing steps taking place in various zones. During normal fixed-bed countercurrent operations, the adsorbent material remains stationary and the individual adsorption, purification, desorption and buffer zones, as defined, are moved through the adsorbent by shifting various input and output streams in a unidirectional manner to allow fluid to flow in a countercurrent direction with respect to solid adsorbent and to continuously produce extract and raffinate streams. In most instances, the shifting of the input and output streams along the fixed bed or adsorbent is done simultaneously and in the same distance along the bed of adsorbent. In other instances, it is desired that two or more zonal functions take place in the adsorbent between two input and output streams before the input and output streams are shifted.

In accordance with the definition of the zones previously given, the adsorption zone I is the adsorbent material located between feed input stream 1 and raffinate output stream 2 which is connected to zone I via line 3. Purification zone IIA is located immediately upstream from adsorption zone I and shares the feed input stream as a common boundary with adsorption zone I. Purification zone IIA is the adsorbent located between the weak desorbent input stream 5 and feed input stream 1. Immediately upstream from the purification zone IIA is purification zone IIB which shares the weak desorbent input stream 5 as a common boundary with purification zone IIA. Purification zone IIB is the adsorbent between extract output stream 4 and weak desorbent input stream 5. Immediately upstream from purification zone IIB is desorption zone III which shares the extract output stream 4 with purification zone IIB as a common boundary. Desorption zone III is the adsorbent between extract output stream 4 and strong desorbent input stream 6. Immediately upstream of desorption zone III is optional buffer zone IVA which shares the strong desorbent inlet stream 6 as a common boundary with desorption zone III and shares flush input stream 7 as a common boundary with a second optional buffer zone IVB. Buffer zone IVA is the adsorbent between the strong desorbent stream 6 and flush input stream 7. Buffer zone IVB is the adsorbent between flush input stream 7 and raffinate output stream 2.

Terminal zones I and IVB are connected by connecting conduits 3 and 8. The connecting conduits allow a portion of the fluid flowing out of zone I via line 3 to eventually flow via line 8 into zone IVB or zone III depending whether or not the optional zone is utilized, thereby, allowing a closed-loop circulation of fluid. Lines 9, 10, 11, 12 and 13 are other connecting conduits connecting, respectively, zones I and IIA, zones IIA and IIB, zones IIB and III, zones III and IVA, zones IVA and IVB to allow a continuous passage of fluid from one zone to and through all the other zones. Specifically, the material passing out of the adsorption zone I via line 3 can pass into line 2 or a portion of it may be diverted via line 8 to be passed eventually into buffer zone IVB. Feedstock which passes into the process via line 1 passes through connecting conduit 9 and into the adsorption zone I. In some instances, a portion of the fluid material which passes out of purification zone IIA via line 9 may pass in admixture with feed material, entering the process via line 1, into adsorption zone I. Line 10 is a connecting conduit through which the fluid material withdrawn from purification zone IIB passes, in admixture with the weak desorbent stream 5, into purification zone IIA. In a similar manner, line 11 connects desorption zone III and purification zone IIB and a portion of the material leaving desorption zone III is allowed to by-pass line 4 and to pass into purification zone IIB. Line 12 connects buffer zone IVA and desorption zone III and permits material passing out of zone IVA to mix with strong desorbent and enter zone III. Line 13 connects buffer zone IVB and zone IVA and a portion of the fluid material leaving buffer zone IVB is allowed to pass out of that zone, to contact material passing into the process via flush input stream line 7 and to pass into the buffer zone IVA. This allows a reduction in process desorbent requirements and removal of $D_s$ from the adsorbent to prevent $D_s$ from entering the raffinate stream. Line 8 can contain a pump or other fluid displacement means in order to induce flow in the process in a direction passing from line 3 through line 8 and into buffer zone IVB.

Other pumps and valves located on the input and output lines and the lines which connect the various zones which control flow into, out of and through the process are not shown. It is presumed they could be located where necessary by one skilled in the art to induce and control proper fluid flow in the process. The input streams passing into the various zones can be connected to high pressure sources or pumping means in order to induce flow into the process and the streams which pass out of the process can be regulated by back pressure valves in order to maintain regulated pressure drops through the zones to induce fluid flow. In some instances unidirectional flow directing devices such as check valves can be located on the conduits between the various zones where a pump around circuit is not utilized.

A feed input stream passes into the process and zone I via line 1 and since the overall general direction of fluid flow within that zone is in a downward direction, passes through line 9 along with any material which may pass out of zone IIA into zone I.

As feed is passed into zone I, an equal volume of raffinate stream material is displaced from zone I leaving that zone via line 3. A portion or all of the raffinate stream which passes through line 3 may be removed from zone I via line 2 with any portion not removed passing through line 8 into either zone III or zone IVB depending upon whether or not optional zone IV is used in the process. Raffinate output stream line 2 is directed to fractionation means 14, hereinafter discussed in more detail, wherein desorbent materials are separated from raffinate components.

The adsorbent in zone I may be envisioned as moving in a direction countercurrent to the fluid flow in the zone. A simulated flow of solids occurs into and out of the adsorption zone when the zones are shifted during a portion of the entire cycle of operations. The adsorbent entering zone I comes from zone III or zone IV depending upon whether or not optional zone IV is used in the process. If optional zone IV is not employed, then the adsorbent leaving zone III and entering zone I will generally contain desorbent materials present in both the non-selective void volumes and the selective void volumes. In instances where zone IV is employed then a portion of the raffinate stream can be passed via line 8 into zone IVB to displace desorbent material from the non-selective void volumes present in the adsorbent particles in zone IVB into zone IVA via line 13. The adsorbent which then passes from buffer zone IVB into adsorption zone I contains for the most part desorbent material located within the adsorbent particle's selective pore volume which the extract material is required to desorb in zone 1. Shown in dotted line 17 the drawing, it is possible to have desorbent material essentially removed from the selective pore volumes by additionally contacting the adsorbent with relatively high purity raffinate material prior to the contacting of the adsorbent with the feed input stream at the upstream portion of the adsorption zone. This feature which is part of a process described in U.S. Pat. No. 3,715,409, is desirable in many systems because it has been found that the absence of desorbent in the adsorption zone enhances the ability of the adsorbent to selectively adsorb and retain the extract component relative to the raffinate component.

The adsorbent, in passing upwardly through the adsorption zone I from its downstream boundary towards its upstream boundary with respect to fluid flow in that zone, adsorbs extract material from the feed input stream. As the adsorbent passes out of the adsorption zone, it contains extract material and some raffinate material located within the selective pore volume of the adsorbent and some raffinate material adsorbed on the adsorbent particle surfaces. The material present in the non-selective void volume of adsorbent is generally raffinate material with small portions of extract material from the feedstock which have not been adsorbed by the adsorbent. This adsorbent then passes into the first purification zone IIA passing into that zone at its downstream boundary feed input stream line.

When the adsorbent passes into the first purification zone IIA from the adsorption zone I, it generally contains some raffinate material present in the adsorbent's selective pore volume, in the non-selective void volume, and adsorbed on the surfaces of the adsorbent particles. The function of purification zone IIA then is to eliminate raffinate material from both the adsorbent's selective pore volume, the adsorbent's non-selective void volume and the adsorbent particle surfaces so that the adsorbent leaving the purification zone via its upstream boundary contains as little raffinate material as possible which could contaminate the extract product stream. These functions are achieved in zone IIA by contacting the adsorbent with a weak desorbent material $D_w$ capable of displacing any raffinate material from the adsorbent's selective pore volume and sweeps displaced raffinate material and raffinate material from the adsorbent's non-selective pore volume downwardly in the descending fluid stream toward the raffinate outlet stream line 3. The weak desorbent stream $D_w$ passes into the purification zone IIA's upstream boundary via lines 5 and 10. When the adsorbent passes into zone IIB from zone IIA, it contains mostly extract material, some weak desorbent material and a very small amount of raffinate material in the adsorbent's selective pore volume and nonselective pore volume. These materials are replaced by a portion of the extract stream, admixture of the strong desorbent and extract materials, passing into purification zone IIB from the desorption zone III via line 11.

The adsorbent which passes out of purification zone IIB passes into desorption zone III. The operation in desorption zone III is essentially the removal of polyunsaturated triglycerides (PUTs), diglycerides and colors from the adsorbent. The removal is effected by contacting the adsorbent with a strong desorbent material ($D_s$) capable of displacing even the 4+ unsaturated PUTs from the selective pore volume of the adsorbent. The strong desorbent enters desorption zone III at its upstream boundary via lines 6 and 12. The strong desorbent carries desorbed PUTs into purification zone IIB. At least a portion of the desorbed PUTs pass out of desorption zone III in admixture with desorbent material mixture via extract output stream line 4. Extract output stream line 4 will then pass to fractionation means 15, hereinafter discussed in more detail, wherein weak desorbent ($D_w$) and PUTs are separated from strong desorbent ($D_s$). The adsorbent leaving desorption zone III contains desorbent material located at both the adsorbent's selective pore volume and non-selective void volume. The adsorbent then passes into optional buffer zone IVA entering zone IVA at its downstream boundary.

Optional zone IV in this process can be used to both conserve the amount of desorbent used in the process and prevent the contamination of extract material by raffinate material components. When operational zone IV is used, it is possible that a portion of the raffinate output stream which does not pass out of line 2 can be passed into zone IVB via lines 3 and 8 to displace desorbent material from the non-selective void volume of the adsorbent particles in zone IVB and push desorbent material out of optional zone IVA via line 12 into zone III. Since the strong desorbent material which passes into the process via line 6 is connected to conduit 12 which connects optional zone IVA with desorption zone III, strong desorbent material $D_s$ which is displaced from the adsorbent in optional zone IVA tends to reduce the requirements of desorbent material which has to pass through line 6 into the process. The solid adsorbent leaving zone IVB at its upstream boundary, the raffinate output stream line 2, contains essentially desorbent material in its selective pore volume with raffinate material present in the adsorbent's non-selective void volume.

In instances in which optional zone IV is not utilized, it is possible to pass some of the raffinate stream from zone 1 directly into zone III. In such instances, it is required that the composition of the material which leaves zone I via line 3 and which bypasses line 2 contains essentially no raffinate material. The initial raffinate material withdrawn from zone I contains a very high concentration of desorbent material and can be passed from lines 3 and 8 into zone III. The flow of raffinate output stream leaving the process via line 2 may be stopped during this. When the stream passing through lines 3 and 8 into zone III contains an appreciable quantity of raffinate material, the flow into zone III via line 8 is stopped and the raffinate output stream is then withdrawn via line 2. While the raffinate materials are being withdrawn through line 2, an outside source of weak desorbent material can be passed into zone IIA via lines 33 and 5.

The input and output lines 1, 2, 4, 5, 6 and 7 during normal operations carry the respective streams as described previously. In order to allow a continuous operation, it is necessary that the individual input and output streams each be shifted in the same direction and in most instances at the same time. By shifting the input and output stream throughout the bed of adsorbent, together with requiring that the terminal zones (adsorption zone I and buffer zone IVB or desorption zone IIIB have a connecting conduit, it is possible to continuously effect the individual operations taking place in the various zones. When the zones described above are being shifted by incremental amounts through stationary adsorbent material, the adsorbent contacts, in the following order, the adsorption zone, the purification zone, the desorption zone and the buffer zone, respectively.

At least a portion of the extract output stream passes through line 4 to fractionation means 15 which is operated at fractionation conditions to produce an overhead stream which is recycled to the strong desorbent input stream line 6 through line 16 and a bottoms stream which passes through line 18.

At least a portion of raffinate output stream passes through line 2 to fractionation means 14 which is operated at fractionation conditions to produce an overhead stream which passes through line 20 and is recycled to the flush input stream via line 7, a sidecut stream which passes through line 21 and a bottoms stream which passes through line 22. The extract and raffinate fractionation columns 14, 15 can be either distillation columns or 2-stage evaporators, the design of which is well known and commonly practiced in this art.

The extract fractionator bottoms stream passes through line 18 to an extract product stripper 19 operated with steam entering line 23. The PUT product (together with contaminants including color bodies, diglycerides, monoglycerides, and unknowns) is taken off the bottom through line 24. Water and $D_w$ are recovered in the overhead through line 25 and pass into a desorbent recovery column 26, normally a fractionator, which removes water via line 27 and returns the weak desorbent via line 28 to the weak desorbent input line 5.

The raffinate fractionator bottoms stream passes through line 22 into a raffinate product stripper 29 operated with steam entering line 30. The MUT product is withdrawn through line 31 and water and weak desorbent $D_w$ are recovered in the overhead 32 and pass into desorbent recovery column 26.

The following examples are illustrative of my invention.

EXAMPLE I

A pulse test, as described above, was performed to evaluate the separation of MUTs from PUTs. The synthetic feed was a mixture comprising 20 wt. % palm olein, 75% desorbent and 5% n-$C_{14}$ (tracer). The palm olein contains 29.1% 1,3-palmitoyl-2-oleyl triglyceride (POP), a monounsaturated triglyceride (MUT), 24.6% 1-palmitoyl-2,3-dioleyl-triglyceride (POO) and minor amount of other polyunsaturated triglycerides and 8.1% unknown impurities plus diglycerides. The adsorbent used was a silver-exchanged aluminosilicate prepared in the manner previously described having the approximate composition by weight: 26% $Ag_2O$; 2% $Na_2O$; 55% $SiO_2$; 19% $Al_2O_3$.

The adsorbent so produced was used to evaluate the ability of the present invention to separate monounsaturated triglycerides (MUTs) from polyunsaturated triglycerides (PUTs) and impurities. For this pulse test, the column was maintained at a temperature of 50° C. and a pressure of 50 psig. Liquid chromatographic analysis equipment was used to analyze the column effluent stream in order to determine the composition of the effluent material at given time intervals. The operations taking place for each test were as follows: The desorbent material was run continuously at a nominal liquid hourly space velocity (LHSV) of 1.3. The desorbent mixture was 25% ethylacetate and 75% n-heptane (n-$C_7$). At some convenient time interval, a pulse of the feed mixture was introduced. The desorbent stream was then resumed at 1.3 LHSV and continued to pass into the adsorbent column until all of the feed components had been eluted from the column as determined by chromatographic analysis of the effluent material leaving the adsorption column. In most cases, the column effluent is analyzed for its various triglyceride components.

Figure 2:
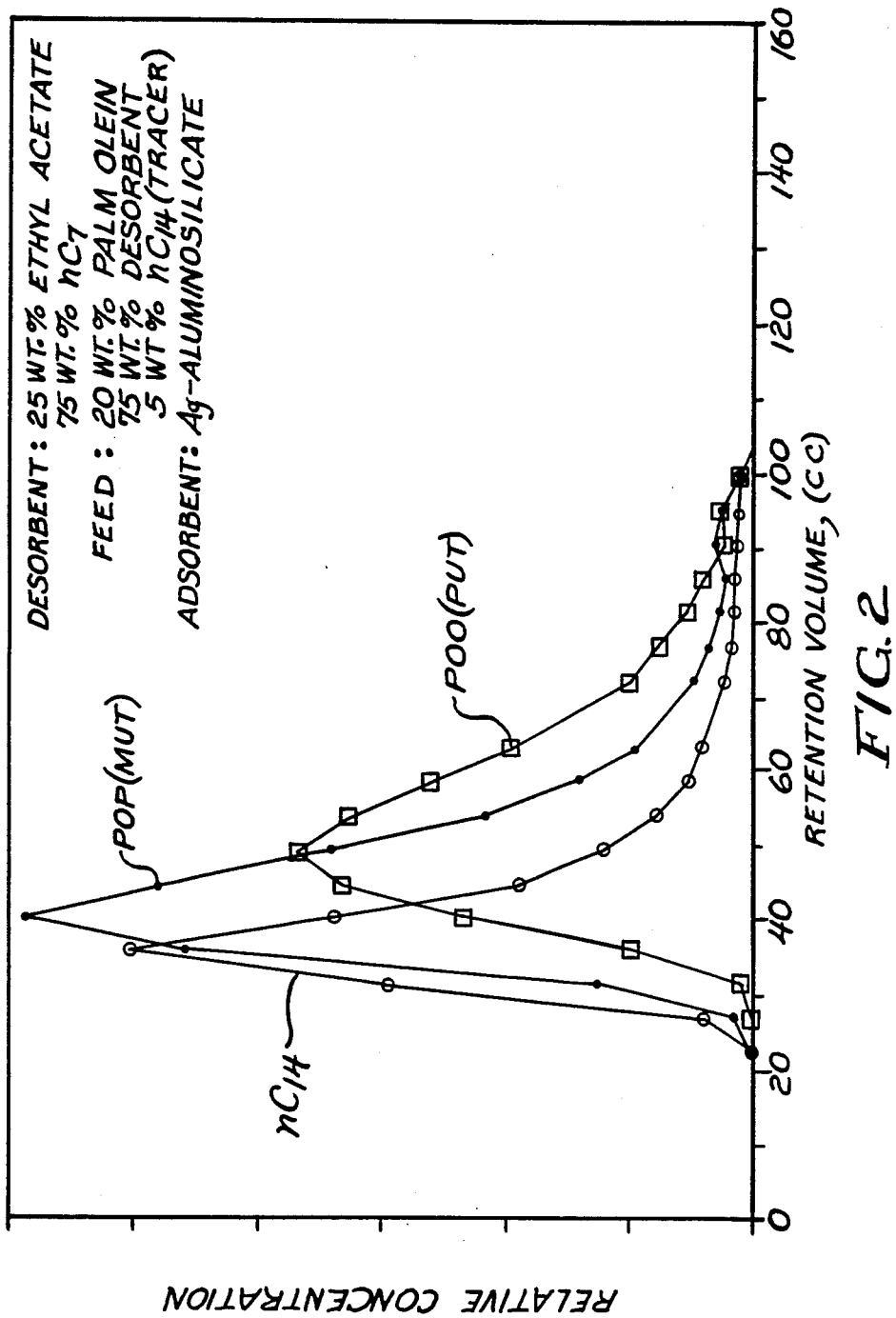

The results of the test of this Example are shown on the accompanying FIG. 2 which comprises the chromatographic trace.

It can be discerned from the test that the separation of POP (MUT) from POO (PUT) is readily achieved by the process of the present invention, with POP eluting as the raffinate. From Equation 1, the selectivity for the POP relative to the POO is 2.9. The retention volume of POO and POP was 14.5 and 5.0 cc, respectively.

In a separate test under similar conditions, the same aluminosilicate adsorbent exchanged with copper ions was used to separate the same feed. Separation was achieved ($\beta = 1.9$), but was not optimized.

EXAMPLE II

The pulse test of Example I was repeated using an identical adsorbent aged with 144 pulses. The results are shown in FIG. 3A.

It can be seen from FIG. 3A (compared with FIG. 2) that the partially deactivated adsorbent of the present invention has reduced selectivity and consequently represents an unacceptable separation. The adsorbent was then regenerated by a treatment with 0.3 wt. % hydrogen peroxide (in aqueous solution) in acetone (99 g acetone; 1 g 30% aqueous solution of $H_2O_2$) and the pulse test rerun. The results are shown in FIG. 3B in which performance is restored to the level of the initial pulse test (FIG. 2).

EXAMPLE III

The pulse test of Example I was repeated using a crude tall oil feed containing 5.4% (wt.) oleic acid (monounsaturated fatty acid) and 12.2% linoleic acid (polyunsaturated fatty acid) and diethyl ketone as desorbent. The separation is shown in FIG. 4, where oleic acid is eluted first (raffinate); and linoleic acid is thereafter removed (extract). The adsorbent was prepared in a manner similar to that of Example I and had a composition of 25.7% $Ag_2O$; 2.0% $Na_2O$; 54.67% $SiO_2$ and 18.7% $Al_2O_3$.

It can be seen from FIG. 4 that the monounsaturated oleic acid is eluted from the column first, whereas the polyunsaturated linoleic acid is eluted later which would result in an extract product enriched in the polyunsaturated acid.

FIGURE IV

Following the procedure outlined for using sequential amounts of two desorbents, namely a first (weak) desorbent, a second (strong) desorbent plus a flush step using weak desorbent, a pulse test was run to separate MUTs from shea butter with an adsorbent prepared in the same manner as that of Example I except that the desorbent was delivered in three steps, as set forth below. The composition of Shea butter is shown in the following Table 1.

TABLE 1

| Component | Wt. % |
|---|---|
| SOS (MUT) | 27.9 |
| Other MUTs (PSO and SOA) | 9.3 |
| SOO (PUT) | 25.7 |
| Other PUTs | 21.9 |
| Unknowns (Total) | 15.3 |
| | 100.1 |

After 67.5 cc of a 5% solution of acetone in n-$C_7$ ($D_w$) have been injected into the column, the desorbent is changed to 100% acetone ($D_s$) until a total of 90 cc has been passed into the column. The desorbent is again changed for the remainder of the pulse test, i.e., until all adsorbed materials have been removed from the adsorbent with weak desorbent $D_w$ (flush) and are eluted from the column. In the first desorption step, the concentration of SOS in the elution liquid is substantially increased over that of the feed to a (raffinate) composition of approximately the following:

TABLE 2

| Component | Wt. % |
|---|---|
| SOS | 75.0 |
| SOO | 15.0 |
| Unknown 1 | 10.0 |

Figure 5:
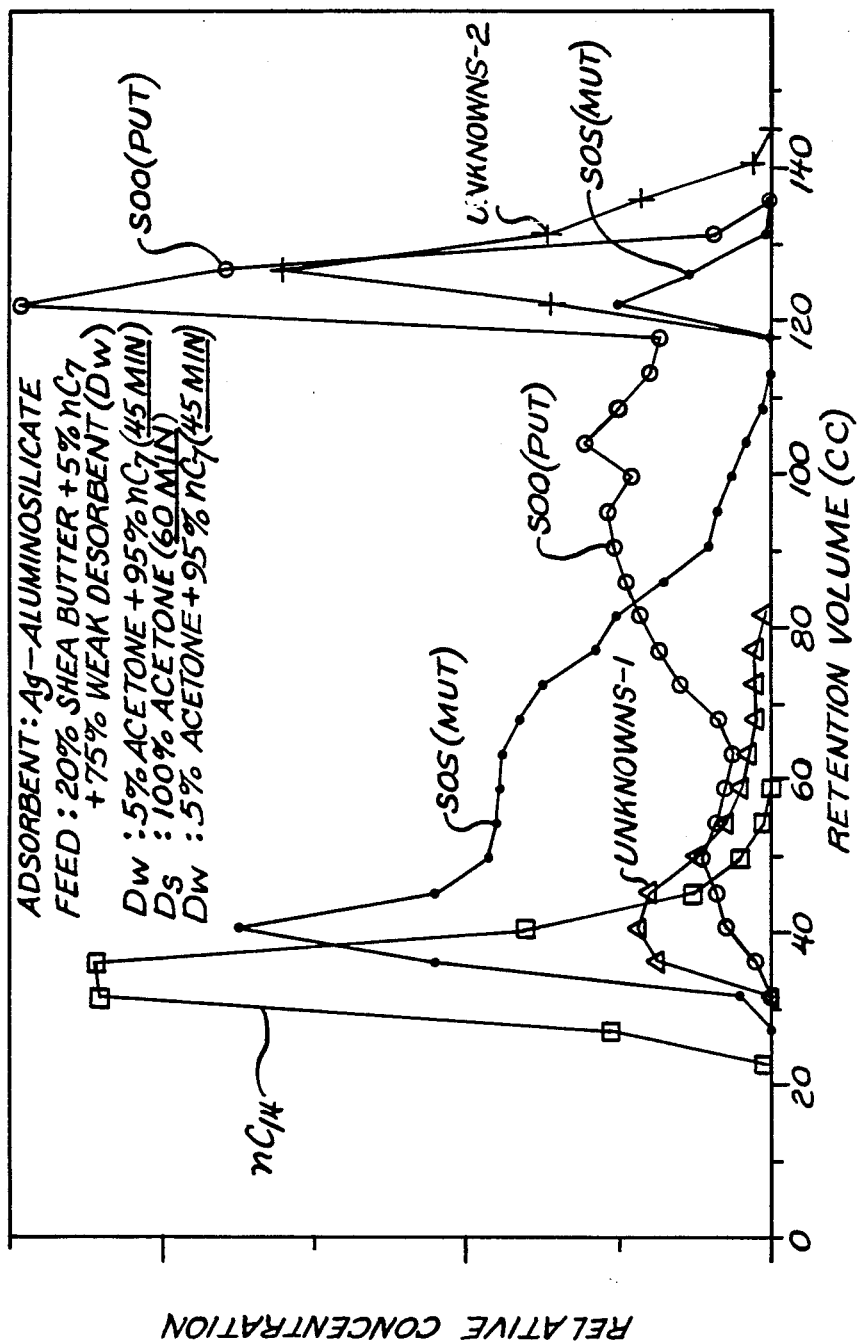

The fraction removed during the second desorption step, representing extract, contains a significant portion of the SOO (PUTs), along with amounts of the other feed material components, and the final fraction of weak desorbent removes the remainder of the adsorbed feed materials from the adsorbent and the strong desorbent. The results of the pulse test are shown in FIG. 5.

EXAMPLE V

Following the same procedure as in Example IV, the palm olein feed of Example I was separated. The adsorbent was prepared in the same manner as that of the previous Example. The weak desorbent and strong desorbent were the same as used in Example IV and for the same durations (45 min.; 60 min., 45 min.). The results of the separation are shown in FIG. 6.

EXAMPLE VI

A pulse test was run in the same manner as Example V on another sample of palm olein having the following composition:

| | |
|---|---|
| POP (MUT) | 32.5% |
| PSO (MUT) | 6.1 |
| PPL (PUT) | 12.8 |
| POO/SOL (PUTs) | 18.8 |
| Other PUTs | 19.0 |
| Unknown | 8.1 |
| Diglycerides | 0.2 |
| PPP (Saturated triglyceride) | 2.5 |
| | 100.0 |

In this Example, the strong desorbent was 99% acetone, 0.3% $H_2O_2$ and 0.7% water. After 18 days (93 bed volumes of feed processed), virtually no deterioration of the adsorbent could be visually detected from a comparison of the pulse test graphs. FIG. 7 is the graph of the pulse test run on the 18th day showing the results of the separation.

EXAMPLE VII

This example illustrates the ability of our process, when operated in the preferred embodiment illustrated in FIG. 1, which utilizes a continuous simulated moving bed countercurrent type of operation, and comprises a pilot plant scale testing apparatus having a swing bed system for regenerating the adsorbent, as described hereinafter. The swing bed system comprises modular units combined into a column with one or more extra modules which can be disconnected from the process during the regeneration. Initially all modules will be loaded with fresh adsorbent. After a period of time, the spent adsorbent in zone IV may be removed from the operation and one of the extra modules inserted in the zone IV position. The adsorbent in the spent module is regenerated by a 1% (wt.) hydrogen peroxide wash without unloading the adsorbent and is then ready for reinsertion back into the process in the zone IV position. Each bed is withdrawn from or inserted into the process in a predetermined sequence by appropriate valving. Briefly, the basic carousel apparatus consists essentially of 24 serially connected adsorbent chambers having about 19.2 cc volume each. Total chamber volume of the apparatus is approximately 460 cc. The individual adsorbent chambers are serially connected to each other with relatively small diameter connecting piping and to a rotary type valve with other piping. The valve has inlet and outlet ports which direct the flow of feed and desorbent material to the chambers and extract and raffinate streams from the chambers. By manipulating the rotary, valve and maintaining given pressure differentials and flow rates through the various lines passing into and out of the series of chambers, a simulated countercurrent flow is produced. The adsorbent remains stationary while fluid flows throughout the serially connected chambers in a manner which when viewed from any position within the adsorbent chambers is steady countercurrent flow. The moving of the rotary valve is done in a periodic shifting manner to allow a new operation to take place in the adsorbent beds located between the active inlet and outlet ports of the rotary valve. Attached to the rotary valve are input lines and output lines through which fluids to and from the process flow. Additional apparatus and general process details can be found in U.S. Pat. No. 3,706,812. In order to better understand the operations taking place within the apparatus reference can be made to D. B. Broughton, U.S. Pat. No. 2,985,589 and to D. B. Broughton et al., "The Separation of P-Xylene from $C_8$ Hydrocarbon Mixtures by Parex Process," presented at the Third Joint Annual Meeting, American Institute of Chemical Engineers and Puerto Rican Institute of Chemical Engineers, San Juan, Puerto Rico, May 17 through May 20, 1970. These references describe in detail the basic operations taking place in the testing apparatus used in this embodiment, and although said references are concerned with the separation of hydrocarbons, the testing apparatus itself is perfectly suited for purposes of this embodiment.

The feed mixture to the apparatus is the palm olein mixture of Example VI. The adsorbent used is also the same. The strong desorbent $D_s$ is 100% acetone; the weak desorbent ($D_w$) is 5% acetone, 95% n-heptane (n-$C_7$).

The operating parameters of the carousel unit are given as follows:

1. A/F=2, where A is the selective pore volume of the adsorbent in cc/hr and F is the feed rate to the separation stage in cc/hr. The selective pore volume is that volume of the adsorbent which has the ability to selectively adsorb one component of a mixture over another.

2. Process temperature=60° C.

3. Valve cycle time=30 min.

4. The ratio of the zone rates ($L_{2A}$, $L_{2B}$ and $L_3$) to selective pore volume (A) are selected on the basis of a process flow mass balance as follows:

$L_{2A}/A=1$ $L_{2B}/B=0.7$ $L_3/A=3.0$

A number of experiments, each of six hours duration, are proposed for the carousel unit in which the PUTs will be adsorbed along with the monoglycerides and diglycerides and separated with the extract, while the MUTs will be relatively unadsorbed and separated in the raffinate. The feed, adsorbent, adsorption conditions and weak and strong desorbents are the same as in Example VI. At 80% MUTs purity, the calculated MUTs recovery is 92%.

Thus, it is clear from the above that the separation of MUTs from a triglyceride mixture containing MUTs and PUTs can be effected with the adsorbent of the invention. Since the effects of different operating conditions on the product purity and yield have not been investigated, the results projected above are not intended to represent the optimums that might be achieved.

What is claimed is:

1. A continuous process for separating monounsaturated triglycerides or fatty acids containing impurities from a feed mixture of monosaturated triglycerides or fatty acids and polyunsaturated triglycerides or fatty acids, said process comprising contacting said feed mixture at adsorption conditions with an adsorbent comprising a silver- or copper exchanged aluminosilicate molecular sieve thereby selectively adsorbing said polyunsaturated triglycerides or fatty acids and desorbing, at desorption conditions, said adosrbed triglycerides or fatty acids with first and second desorbents in sequential steps, said first desorbent comprising a weak desorbent having $S_p$ of from 0.2 to 0.4 and a $S_h$ of from 0.1 to 0.3 and effecting the displacement of the monosaturated triglycerides or fatty acids from said adsorbent and said second desorbent comprising a strong desorbent having a polar component solubility parameter ($S_p$) from 1.3 to 13 and a hydrogen bonding solubility parameter ($S_h$) of from 0.8 to 21 and effecting the displacement of polyunsaturated triglycerides or fatty acids from said adsorbent, said first desorbent selected from the group consisting of normal paraffins and mixtures of normal paraffins and a minor amount of an ester or a ketone or mixtures thereof, said second desorbent comprising a ketone containing from 0.1 to 5 wt. % hydrogen peroxide or an organic peroxide.

2. The process of claim 1 wherein said first desorbent comprises 1–10% of a ketone, an ester or mixtures thereof and said normal paraffin comprises n-heptane.

3. The process of claim 1 wherein said second desorbent material comprises acetone and 0.1 to 0.3 wt. % hydrogen peroxide.

4. The process of claim 1 wherein said adsorption conditions include a temperature within the range of from about 20° C. to about 200° C. and a pressure sufficient to maintain liquid phase.

5. The process of claim 1 wherein monounsaturated triglycerides are separated from a feed mixture comprising monounsaturated triglycerides and polyunsaturated triglycerides.

* * * * *